United States Patent [19]

Purcell et al.

[11] 4,383,252

[45] May 10, 1983

[54] INTRAVENOUS DRIP FEED MONITOR

[76] Inventors: Harold F. Purcell, 419 Old Country Rd., Orange, Conn. 06477; William E. Lattanzi, 834 Dentree Dr., Orange, Conn. 06511; Robert W. Pike, 7998 Island Rd., Eden Prairie, Minn. 55344

[21] Appl. No.: 209,946

[22] Filed: Nov. 24, 1980

[51] Int. Cl.³ .................. G08B 21/00; A61M 5/16
[52] U.S. Cl. .................... 340/606; 128/DIG. 13; 248/75; 248/124; 250/573; 340/609; 604/31; 604/246
[58] Field of Search ............. 340/606, 608, 609, 610, 340/611, 614; 128/214 E, DIG. 13; 250/573; 222/59; 137/486, 487.5; 248/124, 125, 75

[56] References Cited

U.S. PATENT DOCUMENTS

| 2,706,653 | 4/1955 | Blakely | 248/124 X |
|---|---|---|---|
| 2,807,012 | 9/1957 | Schwarz | 340/609 |
| 2,970,798 | 2/1961 | Fritchle et al. | 248/125 X |
| 3,217,542 | 11/1965 | Browning | 248/124 X |
| 3,890,968 | 6/1975 | Pierce et al. | 340/606 X |
| 4,038,982 | 8/1977 | Burke et al. | 250/573 X |

Primary Examiner—John W. Caldwell, Sr.
Assistant Examiner—Daniel Myer
Attorney, Agent, or Firm—Williamson, Bains, Moore & Hansen

[57] ABSTRACT

Intravenous monitor for monitoring drip rate being delivered to a patient from an intravenous solution container and visually displaying the drip rate on a digital readout of the monitor. The monitor includes an alarm for signaling deviations from predetermined adjustable maximum and minimum drip rates. The intravenous monitor includes a photocell reader sensor which positions around a drip chamber below the intravenous container and a horizontal support which maintains vertical orientation of the drip chamber.

8 Claims, 5 Drawing Figures

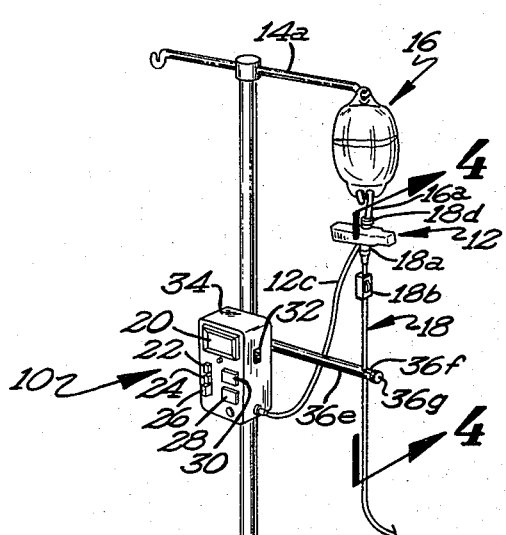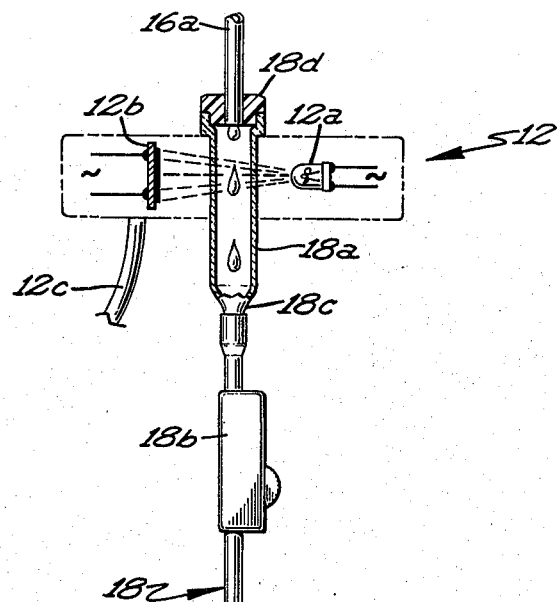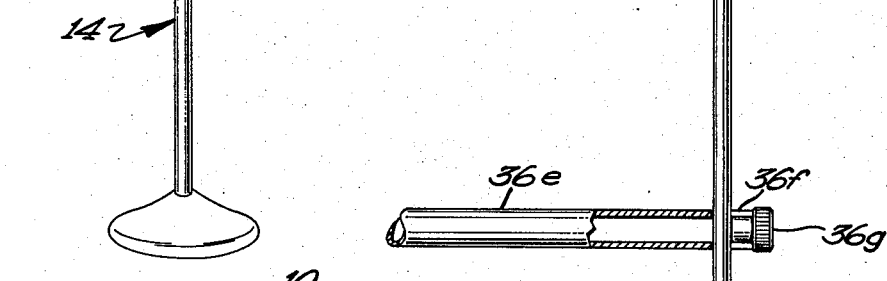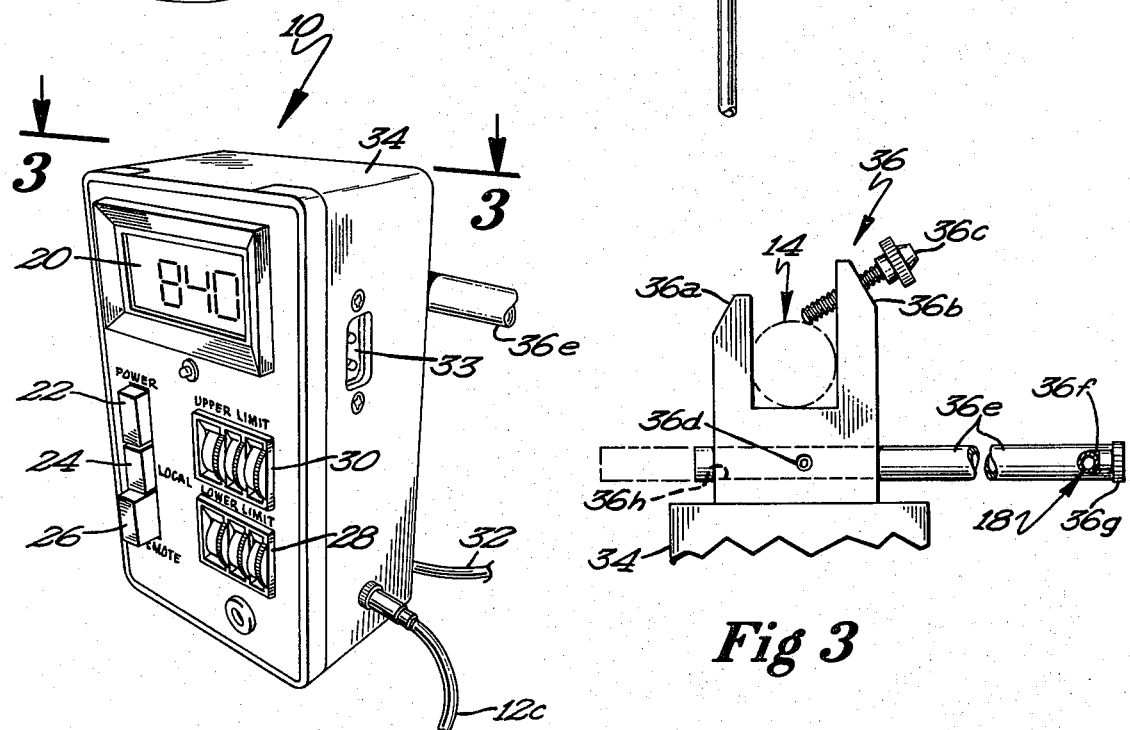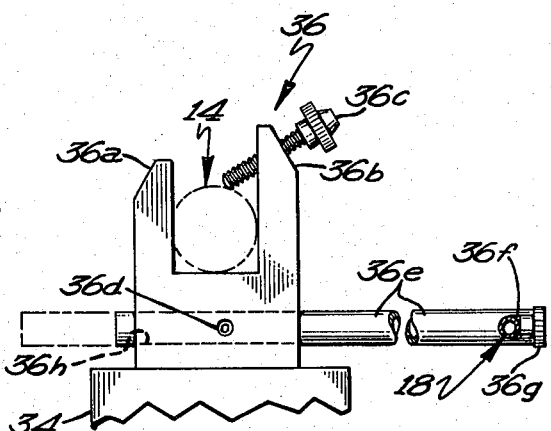

INTRAVENOUS DRIP FEED MONITOR

BACKGROUND OF THE INVENTION

This invention pertains to medical instrumentation, and, more particularly, pertains to an electrical monitor for intravenous (I.V.) drip feeders.

It has been an ever present problem to accurately sense drip rate from an intravenous gravity feed bottle and accurately display the drip rate delivered by fluid therapy administration set-ups. While prior art devices sensed drip rate, the drip rates were not always accurately sensed.

First, the prior art circuits do not provide for fluctuations in the drip rate and frequently have only one alarm condition.

Second, the prior art systems do not provide for ready support of the drip chamber-drip tube in a vertical position, and ready utilization by nursing staff.

Other prior art systems include intravenous mechanical pumps and controllers which are very expensive and usually only used with very critical care patients whose lives may be dependent upon accurate delivery of I.V. fluids in exact accord with their physician's prescriptions. Those systems are very expensive and are only purchased in very limited numbers. The pumps also require use of special, expensive I.V. tubing sets that contain an inline cassette that fits into the pump to accomplish the pumping action.

Representative prior art is U.S. Pat. No. 3,596,515 which illustrates an I.V. stand supporting an intravenous bottle, drip tube, sensor, and monitor. The prior art does not provide for maintaining the drip chamber tube in a substantially vertical position.

The present invention overcomes the deficiencies of the prior art by providing an intravenous administration set alarm monitor which is readily utilized by hospital staff with basic training, and includes adjustable, high and low drip rate alarm settings, visual digital readout of the drip rate, is supported on the standard intravenous stand, and can be used with any standard, gravity feed I.V. tubing set.

SUMMARY OF THE INVENTION

The general purpose of the present invention is an intravenous monitor which monitors the performance of a gravity feed intravenous administration unit displaying a continuously accurate digital readout of the drip rate, and activates an alarm if the drip rate exceeds or falls below limits established and adjustably set by hospital nursing personnel. The intravenous monitor insures patient safety, saves hospital staff time, and contains hospital costs. The intravenous monitor lends itself to ready setup and operation on the intravenous stand, and provides for vertical orientation of the drip chamber in the connected position of the drip tube.

According to one embodiment of the present invention, there is provided an intravenous monitor for mounting on an intravenous stand having an intravenous solution container and tube, the intravenous monitor including a U-shaped bracket supported on an intravenous monitor housing which includes a thumbscrew in one of the legs of the bracket for securing the bracket to the stand, and a horizontal hole extending through the bracket with a setscrew positioned perpendicular thereto for securing a horizontal bar therein and maintaining the drip tube chamber in a vertical position. The housing is connected to the bracket and includes electrical circuitry for visual digital display of the drip rate per minute of the intravenous solution, circuitry for adjustably setting minimum and maximum drip rate alarm levels, circuitry for locating an alarm, either local such as at bedside or remote such as at a nursing station, or both, on sensing a predetermined minimum or maximum drip rate; and circuitry for connecting to a photocell reader sensor, the photocell reader sensor positioning about the vertically oriented drip tube chamber and including a light emitting diode and phototransistors on opposite sides of the light emitting diode for sensing each drip from the I.V. solution container which is coupled to the circuitry in the housing whereby the photocell reader senses each drip which is visually displayed on digital readouts as drops per minute. An alarm is actuated on sensing drip rates which violate predetermined minimum or maximum rates. An adjustable horizontal bar maintains the drip chamber in substantially vertical position to insure that drops fall through the photoelectric field properly.

One significant aspect and feature of the present invention is an intravenous monitor having an adjustable alarm system which alerts hospital personnel to unacceptable deviations from a predetermined prescribed drip rate. The alarm system in effect senses slowdowns, occlusions, runouts, speedups, and runaways. The alarm setting of high drip rate or low drip rate can be adjusted allowing for wide or narrow deviations which would normally be determined by the patient's condition and the intravenous solution being administered.

Another significant aspect and features of the present invention is instant digital visual readout of the drip rate eliminating the need for hospital personnel to time drip rate over a one or two minute period with a watch as customarily done in the past. This feature also eliminates drip rate guestimates which sometimes replace the wrist watch check.

An additional significant aspect and feature of the present invention is a horizontal mounting bracket and bar which maintains the drip chamber and tube in a substantially vertical position from a point below the I.V. container including the drip chambers which prevents tilting the drip chamber by pulling on the drip tube by patient movement. This provides for the highest degree of sensing accuracy by the photocell reader sensor positioned about the drip chamber.

Having thus described the present invention, it is a principal object hereof to provide an intravenous monitor.

An object of the present invention is to visually display on a digital readout the instantaneous drip rate from drop to drop.

Another object of the present invention is an alarm, either local at bedside or remote at a nursing station, which actuates on the drip rate violating a predetermined low or high setting.

A further object of the present invention is a monitor which is capable of operating from AC current or a DC current battery pack.

An additional object of the present invention is a self-contained unit requiring minimal training for operation, and which insures patient safety, saves nursing time, and contains costs. The I.V. monitor is readily set up and placed in operation at patient bedside with but little supervision.

BRIEF DESCRIPTION OF THE DRAWINGS

Other objects and many of the attendant advantages of this invention will be readily appreciated as the same becomes better understood by reference to the following detailed description when considered in connection with the accompanying drawings, in which like reference numerals designate like parts throughout the figures thereof and wherein:

FIG. 1 illustrates a perspective view of an intravenous monitor with a photocell reader positioned on a stand adjacent to a gravity feed intravenous solution container;

FIG. 2 illustrates a perspective view of the intravenous monitor;

FIG. 3 illustrates a sectional view taken along line 3—3 of FIG. 2;

FIG. 4 illustrates a sectional view taken along line 4—4 of FIG. 1; and

DESCRIPTION OF EMBODIMENTS

Figure 5:
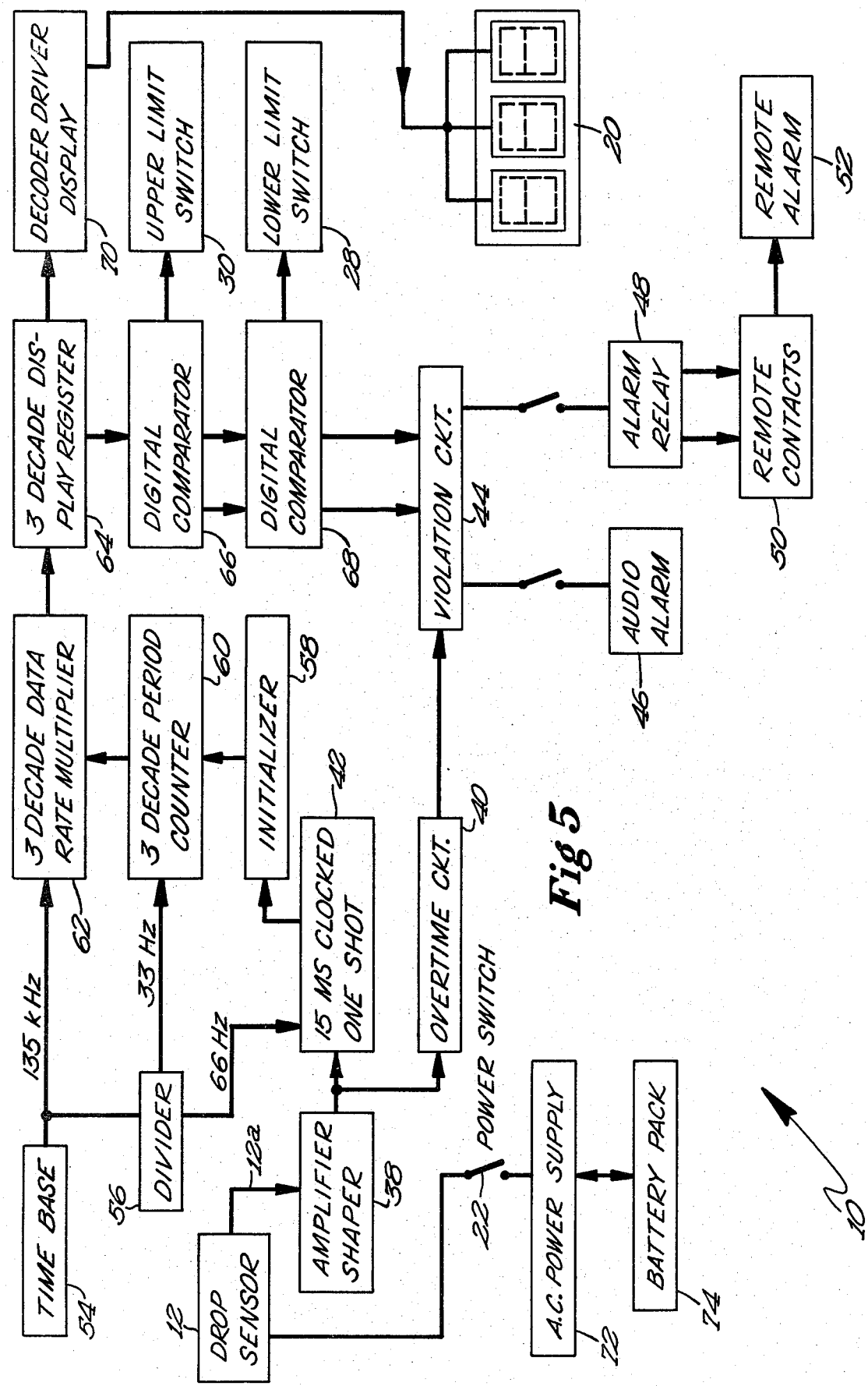
FIG. 5 illustrates an electrical block diagram of the intravenous monitor.

FIG. 1 illustrates a perspective view of an intravenous I.V. monitor 10 with a photocell reader 12 of the present invention positioned on an I.V. stand 14 adjacent to a gravity feed I.V. container 16 including a drip tube 18 and a drip tube chamber 18a. A roller clamp 18b is used on drip tube 18 to initially establish and adjust the drip rate. The I.V. stand 14 includes an upper bracket 14a which supports the I.V. container 16. A lower horizontal rod 36e positions through a bracket 36 as later described in FIG. 3.

FIG. 2, which illustrates a perspective view of the I.V. monitor 10, shows the rod 36e and a cable 12c connecting the I.V. monitor 10 to the photocell reader 12. The I.V. monitor 10 includes a visual digital readout 20, a power on-off switch 22, a local alarm arming switch 24, a remote alarm arming switch 26, a lower drip rate selection switch 28, an upper drip rate selection switch 30, and a power lead 32, all elements being supported in an instrument housing 34. A plug-in connector 33 is utilized for a lead (not shown) electrically connected to the nurses' call station through the patient's call button system.

FIG. 3, which illustrates a sectional view taken along line 3—3 of FIG. 2, shows the horizontal adjustment rod 36e supporting the tube 18, and thereby drip chamber 18a, in a vertical position. Rod 36e is positioned in a bracket 36 secured to the housing 34 of the I.V. monitor 10. The bracket 36 is U-shaped and includes a short leg 36a and a long leg 36b. A threaded thumbscrew 36c screws through an angled end of the long leg 36b and secures the bracket 36 including the housing 34 to the post 14 for height adjustment. A setscrew 36d secures the horizontal adjustment rod 36e engaged in a longitudinal hole 36h which provides for slidable adjustment in a horizontal plane.

FIG. 4, which illustrates a sectional view taken along line 4—4 of FIG. 1, shows the photocell reader 12 including a light emitting diode 12a and an on-axis and two off-axis phototransistors 12b positioned on opposite sides of a transparent drip tube chamber 18a. Drip tube 18 engages over the outflow member 18c of the drip tube chamber 18a. The feed tube 16a from the I.V. container 16 engages into an inflow member 18d of the drip tube chamber 18a. A thumb plug 36g engages the drip tube 18 into the U-shaped end 36f of the horizontal rod 36e as also illustrated in FIG. 3.

FIG. 5 illustrates an electrical circuit block diagram of the I.V. monitor 10. Inside the photocell reader drop sensor 12 is the infrared light emitting diode 12a (LED) which floods the drip chamber 18a with light flux. One on-axis and two off-axis phototransistors 12b receive this light and the output of the transistors 12b partially conducts in the presence of this flux. The effect of the conduction is summed and fed back to the LED in such a way as to establish a sensitive, substantially linear operating point for the sensor 12. Any change in phototransistor conduction due to a passing drop will be reflected to the LED as a significant change in current. In this way, only two wires 12c are required both to power the sensor and to receive the drop signal. The drop signal is capacitively coupled to an amplifier 38 which shapes the incoming signal into a square pulse. When a pulse is received it discharges a capacitor thereby resetting an absolute overtime limit circuit 40. If this circuit has not been reset within substantially 15 seconds by the clocked one shot 42, the violation circuit 44 issues an alarm signal through bistable latch violation circuit 44. If the local alarm 46 and remote alarm 52 have been selected, a continuous tone will sound and a relay 48 pulls in closing a set of remote contacts 50 which are available for remote alarm purposes. Under normal conditions however, a subsequent drop will fall before the above 15 second period. The resultant signal will reset the overtime circuit 40, and will initiate the digital circuit operation through the initializer 58. A continuously running time base 54 establishes through a divider 56 three frequencies: 135 kHz, 66 Hz, 33 Hz. The 66 Hz is used to establish a 15 ms pulse width signal as the result of a drop. At the end of the 15 ms period, a three decade period counter 60 is cleared. Between 15 ms pulses the counter 60 is allowed to accumulate 33 Hz pulses. The count so stored is a measure of the period between drops. At the conclusion of this period, a stream of 2048 pulses (135 kHz for 15 ms) is applied to the input of a variable modulus three decade counter 62. The modulus to be applied has been stored in the first three decade counter 60 described above. The input stream of 2048 pulses is divided by the modulus and is accumulated by the three digit counter 62. This output registers drops per minute. At the end of the 15 ms period, the resulting count is latched and sent to a three digit numerical display 20 by the three decade display register 64 and the decoder driver display 70. The binary coded decimal equivalent of the most significant two digits of this number is also inputted to two, two-digit comparators 66 and 68. The comparison is made to the upper and lower limits set on the front panel digit switches 30 and 28, respectively. If a violation has been determined, the violation circuit 44 is armed. If a second consecutive violation is received, an alarm signal is issued by the violation circuit 46 resulting in the aforementioned alarm response 46. Power is supplied either from an isolated AC source 72 or from an external rechargeable battery pack 74.

MODE OF OPERATION

The intravenous monitor 10 of the present invention is affixed to the post of an I.V. stand with the thumbscrew 36c of the bracket 36. The photocell reader sensor 12 is positioned over the chamber 18a so that the drops fall through between the LED 12a and the transistors 12b. With the power switch 22 off, the unit is plugged into a three wire wall receptacle through power lead 32. The horizontal rod 36e is adjusted to position the drip tube 18 in a vertical position, and is secured by set screw 36d. Plug 36g secures the drip tube 18 in channel 36f of the rod 36e and the horizontal rod 36e is adjusted for substantially vertical orientation of the drip chamber 18a. The sensor 12 is positioned about the drip chamber 18a. By maintaining drip chamber 18a in a substantially vertical position, the possibility of drops running down the side wall of chamber 18a and not being accurately detected by sensor 12 is eliminated.

The upper and lower limit selectors 30 and 28, respectively, are set with the thumb wheel switches for acceptable drops per minute drip rates, taking into account that I.V. rates vary due to movement of the patient, the constantly depleting fluid level in the container, resiliency of the I.V. tubing 18, and other factors. Limits are predetermined to take into account minor drip rate variations, but also for detecting unacceptable speedups and slowdown levels.

The power switch 22 is turned on and the digital readout 20 visually indicates the number of drops per minute. This helps the nurse in the initial establishment of the drip rate.

Local and remote alarms are set by switches 24 and 26, respectively, but the alarms can be defeated by turning off the switches. Local alarm 24 sounds at the bedside monitor 10 and remote alarm 26 can connect to an alarm at a nursing station.

If the minimum lower or maximum upper drip set limits are exceeded twice in succession, the predetermined local and/or remote alarms signal. If no drop falls for any twenty second period, the alarms signal warning of clotting potential. Requiring two successive drip rate violations reduces the potential for false alarms. If the drop conditions self-correct, the alarms automatically shut off.

The unit can also be operated from battery power such as a battery pack 74.

Various modifications can be made to the intravenous monitor of the present invention without departing from the apparent scope thereof.

What is claimed is:

1. Intravenous monitor apparatus for use with an intravenous pole stand supporting an intravenous solution container having a drip chamber and a drip tube extending downwardly therefrom, comprising:
    a mounting bracket including means for releasably securing said bracket to said intravenous pole stand for vertical adjustment thereon, and having horizontally elongated guide means integral therewith;
    a horizontal bar slidably supported within said elongated guide means and longitudinally adjustable therein, said bar including means thereon remote from said mounting bracket for restrainably engaging a segment of said drip tube at a desired horizontal distance from said pole stand below said drip chamber, and releasable retention means on said bracket holding said bar in said elongated guide means;
    means positioned in proximity to said drip chamber for sensing each intravenous drip and generating a signal in response to each drip; and
    an intravenous monitor in a housing affixed to said bracket and including circuit means within said housing electrically connected to said drip sensing means and operative to process said signals, and means within said monitor housing connected to said circuit means for visual display numerically of the drip rate as counted by said signal processing means, whereby said bracket vertically positions said intravenous monitor on said intravenous pole stand and said adjustable horizontal bar engaged through said bracket provides for substantial vertical orientation of said drip chamber, thereby providing for accuracy of said visually displayed drip rate.

2. Intravenous monitor apparatus as defined in claim 1 wherein:
    said mounting bracket is a U-shaped member defined by a base and a pair of spaced apart legs extending therefrom, and said means releasably securing said bracket to said pole stand comprises friction contact means on one of said legs releasably engaging said pole stand with said pole stand positioned between said legs.

3. Intravenous monitor apparatus as defined in claim 2 wherein:
    said horizontally elongated guide means comprises an elongated aperture extending substantially horizontally through said base of said bracket between the pole receiving space between said bracket legs and said monitor housing.

4. Intravenous monitor apparatus as defined in claim 3 wherein:
    said releasable retention means on said bracket holding said bar comprises a releasable, threaded member extending through said bracket base and engaging said bar in said elongated aperture.

5. Intravenous monitor apparatus as defined in claim 2 wherein:
    said friction contact means comprises an elongated, threaded member extending through one of said bracket legs at an acute angle with respect thereto, said threaded member being angled towards the other bracket leg and said base to hold said pole stand securely thereagainst.

6. Intravenous monitor apparatus as defined in claim 1 wherein:
    said intravenous monitor comprises means for setting a predetermined minimum drip rate, means for setting a predetermined maximum drip rate, and means for initiating an alarm when the drip rate exceeds said maximum or falls below said minimum drip rate.

7. Intravenous monitor apparatus as defined in claim 6 wherein:
    said circuit means comprises means for sensing two consecutive violations of the maximum or minimum drip rate settings, and means for indicating an alarm on twice consecutively sensing such violations.

8. Intravenous monitor apparatus as defined in claim 1 wherein:
    said sensing means comprises a light emitting diode-phototransistor assembly disposed on opposite sides of said drip chamber.

* * * * *